United States Patent
Schultz

(10) Patent No.: US 10,611,986 B1
(45) Date of Patent: Apr. 7, 2020

(54) CLEANING COMPOSITION COMPRISING A CATIONIC/NONIONIC MIXTURE

(71) Applicant: Earthcare Labs, LLC, Los Angeles, CA (US)

(72) Inventor: Gary E. Schultz, Los Angeles, CA (US)

(73) Assignee: Earthcare Labs, LLC, Los Angeles, CA (US)

( * ) Notice: Subject to any disclaimer, the term of this patent is extended or adjusted under 35 U.S.C. 154(b) by 0 days.

(21) Appl. No.: 16/352,036

(22) Filed: Mar. 13, 2019

Related U.S. Application Data

(60) Provisional application No. 62/643,648, filed on Mar. 15, 2018.

(51) Int. Cl.

| | | |
|---|---|---|
| C11D 1/86 | (2006.01) | |
| C11D 1/835 | (2006.01) | |
| C11D 3/22 | (2006.01) | |
| C11D 3/32 | (2006.01) | |
| C11D 3/30 | (2006.01) | |
| C11D 3/20 | (2006.01) | |
| C11D 3/33 | (2006.01) | |
| C11D 3/43 | (2006.01) | |

(52) U.S. Cl.
CPC ............ *C11D 1/835* (2013.01); *C11D 3/2093* (2013.01); *C11D 3/222* (2013.01); *C11D 3/30* (2013.01); *C11D 3/323* (2013.01); *C11D 3/33* (2013.01); *C11D 3/43* (2013.01)

(58) Field of Classification Search
CPC combination set(s) only.
See application file for complete search history.

(56) References Cited

U.S. PATENT DOCUMENTS

| | | | |
|---|---|---|---|
| 3,287,214 A | 11/1966 | Taylor et al. | |
| 3,969,500 A | 7/1976 | Kennerley | |
| 4,851,214 A | 7/1989 | Walters et al. | |
| 5,039,363 A | 8/1991 | Jo et al. | |
| 5,080,831 A * | 1/1992 | VanEenam | C11D 3/43 510/272 |
| 5,198,209 A | 3/1993 | Zhou et al. | |
| 5,344,643 A | 9/1994 | Thiel et al. | |
| 5,942,086 A | 8/1999 | Owen | |
| 6,069,140 A | 5/2000 | Sessler et al. | |
| 6,491,902 B2 | 12/2002 | Shefer et al. | |
| 7,878,644 B2 | 2/2011 | Meyers et al. | |
| 7,896,485 B2 | 3/2011 | Lafleche et al. | |
| 8,092,854 B2 | 1/2012 | Toreki et al. | |
| 9,895,413 B2 | 2/2018 | Awasthi et al. | |
| 2002/0022660 A1 * | 2/2002 | Jampani | A61K 36/899 514/635 |
| 2002/0086039 A1 * | 7/2002 | Lee | A61K 8/22 424/401 |
| 2003/0034248 A1 | 2/2003 | Kaylo | |
| 2003/0093946 A1 | 5/2003 | Gutierrez Pavez | |
| 2004/0251190 A1 | 12/2004 | Cumberland | |
| 2005/0261154 A1 | 11/2005 | Hammock | |
| 2006/0147505 A1 | 7/2006 | Tanzer et al. | |
| 2007/0110958 A1 | 5/2007 | Meyers et al. | |
| 2007/0167347 A1 | 7/2007 | Gallotti et al. | |
| 2007/0173426 A1 | 7/2007 | Longoria et al. | |
| 2007/0275021 A1 * | 11/2007 | Lee | A61K 8/22 424/401 |
| 2008/0233062 A1 | 9/2008 | Krishnan | |
| 2008/0275113 A1 * | 11/2008 | Huetter | A01N 25/30 514/494 |
| 2010/0009366 A1 | 1/2010 | Kerb et al. | |
| 2010/0267598 A1 * | 10/2010 | Sans | A61K 8/345 510/130 |
| 2010/0284955 A1 | 11/2010 | Lepilleur et al. | |
| 2011/0189247 A1 | 8/2011 | Glenn, Jr. et al. | |
| 2011/0245339 A1 | 10/2011 | Ganapathy et al. | |
| 2012/0128650 A1 | 5/2012 | Bragger et al. | |
| 2012/0214590 A1 | 8/2012 | Newhouse et al. | |
| 2012/0328720 A1 * | 12/2012 | West | A23L 2/02 424/732 |
| 2015/0167246 A1 | 6/2015 | Cusola Aumedes et al. | |
| 2016/0095804 A1 * | 4/2016 | Xavier | A61K 8/44 510/127 |
| 2016/0115194 A1 | 4/2016 | Gagnon | |
| 2017/0369818 A1 * | 12/2017 | Park | C11D 1/83 |
| 2018/0064838 A1 * | 3/2018 | Blondeau | A61L 9/012 |
| 2018/0086740 A1 | 3/2018 | Liu | |
| 2018/0228718 A1 * | 8/2018 | Nguyen | A61K 8/342 |
| 2019/0125634 A1 * | 5/2019 | Linder | A01N 25/16 |
| 2019/0191704 A1 * | 6/2019 | Albright | A01N 47/44 |

OTHER PUBLICATIONS

Cornell University Cooperative Extension, Agronomy Fact Sheet Series, Fact Sheet 22, Cation Exchange Capacity (CEC), Department of Crop and Soil Sciences, College of Agriculture and Life Sciences, pp. 1-2, (2007).

* cited by examiner

*Primary Examiner* — Charles I Boyer
(74) *Attorney, Agent, or Firm* — Knobbe, Martens, Olson & Bear LLP

(57) ABSTRACT

Disclosed herein are cleaning compositions including water, at least one cationic surfactant, and at least one nonionic surfactant.

21 Claims, 14 Drawing Sheets

FIG. 1:

Example anionic surfactants:

- Ammonium lauryl sulfate
- Sodium dodecyl sulfate
- Sodium lauryl sulfate
- Sodium coco-sulfate
- Sodium coco-sulfate
- Ammonium laureth sulfate
- Sodium laureth sulfate
- Triethanolamine lauryl sulfate
- Sodium lauroyl sarcosinate
- Sodium lauryl sulfoacetate
- Sodium stearoyl lactylate
- Sodium isostearoyl lactylate
- Sodium lauroyl isethionate
- Sodium cocoyl isethionate
- Disodium lauroaphodiacetate
- Disodium coco-glucoside citrate
- Sodium lauryl glucose carboxylate
- Sodium laurylglucosides hydroxypropylsulfonate
- Sodium methyl cocoyl taurate
- Sodium dodecylbenzenesulfonate
- Fatty acyl isethionates
- Fatty acyl taurates
- Fatty acyl sulfosuccinates
- Alkanoyl glycinates
- Alkanoyl sarcosinates

FIG. 2:

Example nonionic surfactants:

- Lauryldimethylamine oxide
  - Lauramine oxide
- Fatty alcohol polyglycol ethers
  - Ceteareth-3
  - Ceteareth-6
  - Ceteareth-12
  - Ceteareth-20
  - Ceteareth-30
  - Ceteth-1
  - Ceteth-2
  - Ceteth-3
  - Ceteth-5
  - Ceteth-7
  - Ceteth-8 Phosphate
  - Ceteth-10
  - Ceteth-15
  - Ceteth-24
  - Laureth-2
  - Laureth-3
  - Laureth-4
  - Laureth-6
  - Laureth-8
  - Laureth-15
  - Laureth-21
  - Laureth-23
  - Laureth-30
  - Trideceth-3
  - Trideceth-7
  - Trideceth-8
  - Trideceth-9
  - Trideceth-10
  - Trideceth-12
- Cocamide DEA
- Cocamidopropyl betaine
- Laramide DEA
- Hydroxysultaine
  - Cocamidopropyl hydroxysultaine
- Decyl glucoside
- Lauryl glucoside
- Coco glucoside
- Maltooligosyl glucoside
- Glyceryl cocoate
  - PET-7 Glyceryl cocoate
  - PEG-40 Glyceryl cocoate
- Sorbital- and Sorbitan-based nonionic surfactants
  - Polysorbate-20
  - Polysorbate-60
  - Polysorbate-61
  - PEG-80 sorbitan laurate

FIG. 4A:

EXAMPLE FABRIC CLEANING COMPOSITION

| Component Number | Component Description | Weight |
|---|---|---|
| 1 | Soft water | 70.0 to 74.0 wt% |
| 2 | Hydroxyethylcellulose | 0.1 to 5.0 wt% |
| 3 | Cetyl hydroxyethylcellulose | 0.1 to 5.0 wt% |
| 4 | Diammonium EDTA | 0.1 to 5.0 wt% |
| 5 | Quaternium-A*;** | 0.05 to 5.0 wt% |
| 6 | Benzethonium chloride** | 0.1 to 5.0 wt% |
| 7 | Cocamidopropyl hydroxysultaine | 0.1 to 5.0 wt% |
| 8 | Soyethyl morpholinium ethosulfate** | 0.05 to 5.0 wt% |
| 9 | Cocamine oxide | 0.1 to 7.0 wt% |
| 10 | Soft water | 8.0 to 12.0 wt% |
| 11 | Quaternium-A*;** | 0.05 to 5.0 wt% |
| 12 | Allantoin | 0.1 to 4.0 wt% |
| 13 | Polyquaternium-10 | 0.1 to 5.0 wt% |
| 14 | Hexylene glycol | 0.1 to 5.0 wt% |
| 15 | Isoamyl acetate | 0.05 to 5.0 wt% |
| 16 | Hexyl acetate | 0.05 to 5.0 wt% |

*a,a'-[[Methyl[3-(tridecyloxy)propyl]iminio]di-2,1-ethanediyl][bis][w-hydroxy-poly(oxy-1,2-ethanediyl)] chloride

**Antimicrobial/preservative

Directions:
1. Mix components #1-3 at high sheer for 30 minutes, let stand.
2. Add components #4-9 each to the thickener solution above, with stirring.
3. Premix components #10-16 and add with stirring.
4. Adjust pH to 4.5 with HCl

FIG. 4B:

EXAMPLE SHAMPOO COMPOSITION

| Component Number | Component Description | Weight |
|---|---|---|
| 1 | Soft water | 70.0 to 74.0 wt% |
| 2 | Hydroxyethylcellulose | 0.1 to 5.0 wt% |
| 3 | Cetyl hydroxyethylcellulose | 0.1 to 5.0 wt% |
| 4 | Diammonium EDTA | 0.1 to 5.0 wt% |
| 5 | Benzethonium chloride* | 0.1 to 5.0 wt% |
| 6 | Cocamidopropyl hydroxysultaine | 0.1 to 10.0 wt% |
| 7 | Soyethyl morpholinium ethosulfate* | 0.05 to 5.0 wt% |
| 8 | Cocamine oxide | 1.0 to 10.0 wt% |
| 9 | Soft water | 8.0 to 12.0 wt% (q.s. to 100%) |
| 10 | Allantoin | 0.1 to 5.0 wt% |
| 11 | Polyquaternium-10 | 0.1 to 5.0 wt% |
| 12 | Lauryl glucoside | 0.1 to 7.0 wt% |
| 13 | Maltooligosyl glucoside | 0.1 to 5.0 wt% |
| 14 | Guar hydroxypropyltrimonium chloride | 0.1 to 5.0 wt% |
| 15 | D-Panthenol | 0.1 to 5.0 wt% |
| 16 | Polyquaternium-70 | 0.1 to 5.0 wt% |
| 17 | Behentrimonium methosulfate | 0.0 to 10.0 wt% |
| 18 | Acetamide MEA | 0.1 to 5.0 wt% |
| 19 | Acetamidopropyltrimonium chloride | 0.1 to 5.0 wt% |
| 20 | Hexylene glycol | 0.0 to 10.0 wt% |
| 21 | Isoamyl acetate | 0.0 to 5.0 wt% |
| 22 | Hexyl acetate | 0.0 to 5.0 wt% |
| 23 | Coco-glucoside | 0.0 to 10.0 wt% |
| 24 | Glycol distearate | 0.0 to 10.0 wt% |
| 25 | Natural Essences | 0.0 to 10.0 wt% |

*Antimicrobial/preservative

Directions:
1. Mix components #1-3 at high sheer for 30 minutes, let stand.
2. Add components #4-8 each to the solution above, with stirring.
3. Premix components #9-11 and add with stirring.
4. Add components #12-25 each to the solution above, with stirring.
5. Homogenize solution.
6. Adjust pH to 4.5 with HCl

FIG. 4C:

ANOTHER EXAMPLE SHAMPOO COMPOSITION

| Component Number | Component Description | Weight |
|---|---|---|
| 1 | Soft water | 70.0 to 74.0 wt% |
| 2 | Hydroxyethylcellulose | 0.5 to 5.0 wt% |
| 3 | Cetyl hydroxyethylcellulose | 0.25 to 5.0 wt% |
| 4 | Diammonium EDTA | 1.0 to 5.0 wt% |
| 5 | Benzethonium chloride* | 0.1 to 5.0 wt% |
| 6 | Cocamidopropyl hydroxysultaine | 0.1 to 10.0 wt% |
| 7 | Soyethyl morpholinium ethosulfate* | 0.05 to 5.0 wt% |
| 8 | Cocamine oxide | 1.0 to 10.0 wt% |
| 9 | Soft water | 8.0 to 12.0 wt% (q.s. to 100%) |
| 10 | Allantoin | 0.1 to 5.0 wt% |
| 11 | Polyquaternium-10 | 0.1 to 5.0 wt% |
| 12 | Lauryl glucoside | 0.1 to 7.0 wt% |
| 13 | Maltooligosyl glucoside | 0.1 to 5.0 wt% |
| 14 | Guar hydroxypropyltrimonium chloride | 0.1 to 5.0 wt% |
| 15 | D-Panthenol | 0.1 to 5.0 wt% |
| 16 | Polyquaternium-70 | 0.1 to 5.0 wt% |
| 17 | Behentrimonium methosulfate | 0.0 to 10.0 wt% |
| 18 | Acetamide MEA | 0.1 to 5.0 wt% |
| 19 | Acetamidopropyltrimonium chloride | 0.1 to 5.0 wt% |
| 20 | Hexylene glycol | 0.0 to 10.0 wt% |
| 21 | Isoamyl acetate | 0.0 to 5.0 wt% |
| 22 | Hexyl acetate | 0.0 to 5.0 wt% |
| 23 | Natural Essences | 0.0 to 10.0 wt% |

*Antimicrobial/preservative

Directions:
1. Mix components #1-3 at high sheer for 30 minutes, let stand.
2. Add components #4-8 each to the solution above, with stirring.
3. Premix components #9-11 and add with stirring.
4. Add components #12-23 each to the solution above, with stirring.
5. Homogenize solution.
6. Adjust pH to 6.5 with HCl

FIG. 4D:

EXAMPLE BODY WASH COMPOSITION

| Component Number | Component Description | Weight |
|---|---|---|
| 1 | Soft water | 70.0 to 74.0 wt% |
| 2 | Hydroxyethylcellulose | 0.1 to 5.0 wt% |
| 3 | Cetyl hydroxyethylcellulose | 0.1 to 5.0 wt% |
| 4 | Diammonium EDTA | 1.0 to 5.0 wt% |
| 5 | Benzethonium chloride* | 0.1 to 5.0 wt% |
| 6 | Cocamidopropyl hydroxysultaine | 0.1 to 10.0 wt% |
| 7 | Soyethyl morpholinium ethosulfate* | 0.05 to 5.0 wt% |
| 8 | Cocamine oxide | 1.0 to 10.0 wt% |
| 9 | Soft water | 8.0 to 12.0 wt% (q.s. to 100%) |
| 10 | Allantoin | 0.1 to 5.0 wt% |
| 11 | Polyquaternium-10 | 0.1 to 5.0 wt% |
| 12 | Lauryl glucoside | 0.1 to 7.0 wt% |
| 13 | Maltooligosyl glucoside | 0.1 to 5.0 wt% |
| 14 | Guar hydroxypropyltrimonium chloride | 0.1 to 5.0 wt% |
| 15 | D-Panthenol | 0.1 to 5.0 wt% |
| 16 | Hexylene glycol | 0.0 to 10.0 wt% |
| 17 | Isoamyl acetate | 0.0 to 5.0 wt% |
| 18 | Hexyl acetate | 0.0 to 5.0 wt% |
| 19 | Natural Essences | 0.0 to 10.0 wt% |

*Antimicrobial/preservative

Directions:
1. Mix components #1-3 at high sheer for 30 minutes, let stand.
2. Add components #4-8 each to the solution above, with stirring.
3. Premix components #9-11 and add with stirring.
4. Add components #12-19 each to the solution above, with stirring.
5. Homogenize solution.
6. Adjust pH to 4.5 with HCl

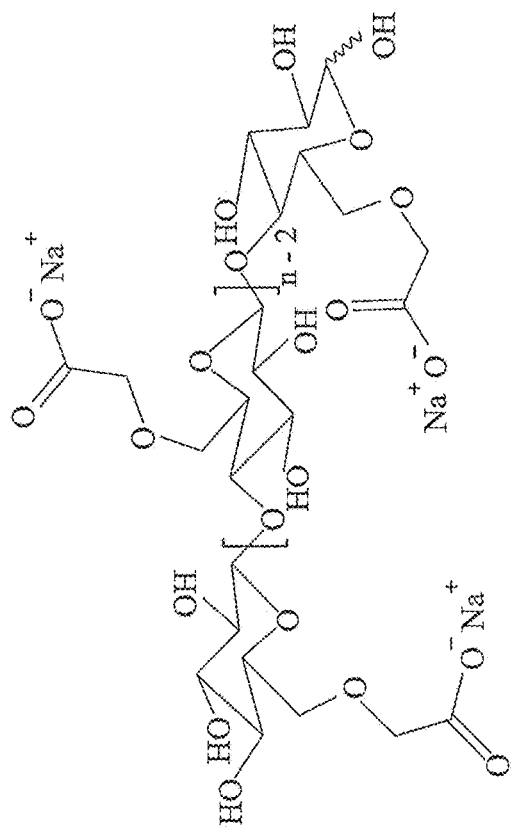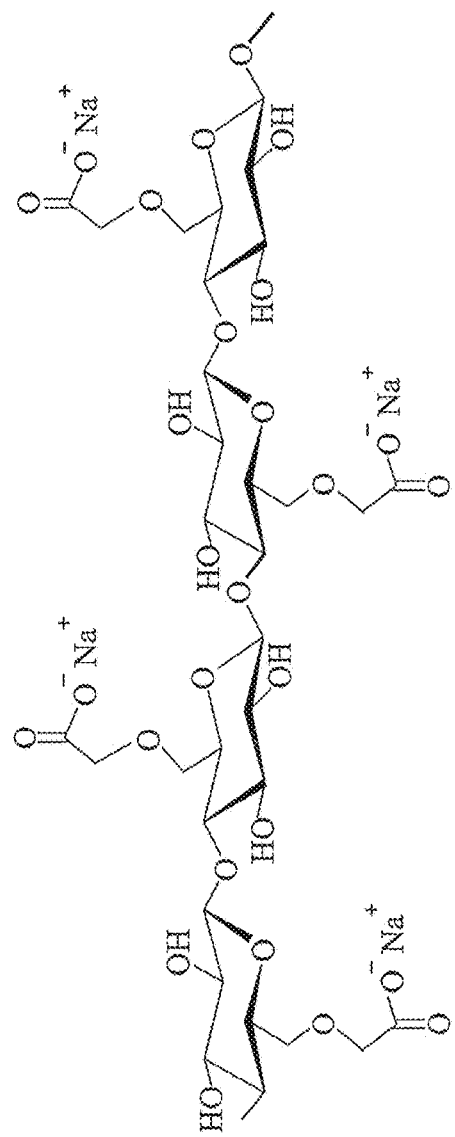
FIG. 6:

CLEANING COMPOSITION COMPRISING A CATIONIC/NONIONIC MIXTURE

CLAIM OF PRIORITY

This application claims the benefit of priority to U.S. Provisional Appl. No. 62/643,648, filed Mar. 15, 2018, which is incorporated in its entirety by reference herein.

BACKGROUND

Field

The present application relates to the field of cleaning compositions. More particularly, disclosed herein are compositions and ingredients of said compositions for cleaning textiles and clothes and for use as shampoos for humans and/or animals. Also disclosed herein are methods of making such compositions.

Description of the Related Art

Traditional cleaning compositions, particularly commercial laundry detergents and soaps available in the marketplace, function as substances that physically remove dirt, soil and stains from the textile surfaces being cleaned. In general, laundry detergents contain water softeners, surfactants, bleach, enzymes, brighteners, fragrances and many other agents. The major components of laundry detergents include anionic surfactants, alkaline builders, water softening agents and anti-redeposition agents. Higher end detergents contain enzymes and optical brighteners. Some liquid detergents contain nonionic surfactants.

Many kinds of molecules and ions can serve as high-efficiency surfactants. They are often classified according to the charge of the molecule or ion, the three main classes being anionic, neutral and cationic. Anionic surfactants are most commonly encountered for domestic laundry detergents. Detergents are ions or molecules that contain both polar and nonpolar components. The polar components ("hydrophilic") allow the detergent to dissolve in the water, whereas the nonpolar components solubilize greasy ("hydrophobic") materials that are the usual target of the cleaning process. The surfactants physically incorporate (dissolve) the dirt, oil, or stains in their micelles and then transport them away from the textile surfaces and into the bulk of the cleaning liquid.

Many other ingredients can be added depending on the specific application. Certain additives can be added to modify the foaming properties of the product by either stabilizing or counteracting foam. Other ingredients can be added to increase or decrease the viscosity of the solution, or to solubilize other ingredients. Corrosion inhibitors can be added to counteract damage to washing equipment. "Dye transfer inhibitors" can be added to prevent dyes from one article from coloring other items. "Anti-redeposition agents" can be added to prevent fine soil particles from reattaching to the product being cleaned.

SUMMARY

In some embodiments, a cleaning composition comprises water, at least one cationic surfactant and at least one nonionic surfactant; and wherein the at least one cationic surfactant is selected from the group consisting of Polyquaternium-1, Polyquaternium-4, Polyquaternium-6, Polyquaternium-10, Polyquaternium-11, Polyquaternium-12, Polyquaternium-15, Polyquaternium-16, Polyquaternium-18, Polyquaternium-20, Polyquaternium-30, Polyquaternium-43, Polyquaternium-51, Polyquaternium-57, Polyquaternium-67, Polyquaternium-22, Polyquaternium-37, Polyquaternium-44, Polyquaternium-52, Polyquaternium-59, Polyquaternium-68, Polyquaternium-24, Polyquaternium-38, Polyquaternium-46, Polyquaternium-53, Polyquaternium-64, Polyquaternium-69, Polyquaternium-28, Polyquaternium-39, Polyquaternium-47, Polyquaternium-55, Polyquaternium-65, Polyquaternium-70, Polyquaternium-72, Polyquaternium-73, Polyquaternium-76, Polyquaternium-80, Quaternium-15, Quaternium-26, Quaternium-33, Quaternium-70, Quaternium-75, Quaternium-79, Quaternium-82, Quaternium-83, Quaternium-84, Quaternium-89, Quaternium-90, Quaternium-91, Quaternium-95, Benzethonium chloride, Quaternium-Λ, Benzalkonium chloride, behentrimonium methosulfate, behentrimonium chloride, acetamidopropyltrimonium chloride, guar hydroxypropyltrimonium chloride, soyethyl morpholinium ethosulfate and cocamine oxide; and wherein the at least one nonionic surfactant is selected from the group consisting of cetyl hydroxyethylcellulose, cocamidopropyl hydroxysultaine, lauryl hydroxysultaine, coconut fatty alcohol polyglycol ethers with ethylene oxide (EO) units ranging between 2 and 30, C8-C22 alkyl glucosides, for example decyl glucoside, lauryl glucoside, coco glucoside and maltooligosyl glucoside; C8-C16 alkyl polyglucosides for example oligomeric D-glucopyranose and C8-C16 alkyl glycosides, C8-C22 alkyl maltosides, for example n-dodecyl-β-D-maltopyranoside (DDM), cocamide MIPA and cocamide DIPA. In certain embodiments, the composition contains substantially no anionic surfactants (e.g., an anionic surfactant component of the composition comprises less than 1 wt. % of the total weight of the composition).

In some embodiments, the cleaning composition further comprises at least one thickening agent. In some embodiments, the cleaning composition further comprises at least one foaming agent. In some embodiments, the cleaning composition further comprises at least one foam conditioning agent. In some embodiments, the cleaning composition further comprises at least one skin conditioner. In some embodiments, the cleaning composition further comprises at least one fragrance agent. In some embodiments, the water of the cleaning composition is a solvent and the cleaning composition further comprises at least one co-solvent. In some embodiments, the cleaning composition further comprises at least one chelating agent. In some embodiments, the cleaning composition further comprises at least one deodorizing agent.

BRIEF DESCRIPTION OF THE DRAWINGS

FIG. 1 shows a listing of some example anionic surfactants in accordance with certain embodiments described herein.

FIG. 2 shows a listing of some example nonionic surfactants in accordance with certain embodiments described herein.

FIGS. 4A-4D shows various example compositions in accordance with certain embodiments described herein.

FIG. 6 schematically illustrates sodium carboxymethyl cellulose (SCMC), which can be used as an anti-redeposition agent.

DETAILED DESCRIPTION

Figure 3:
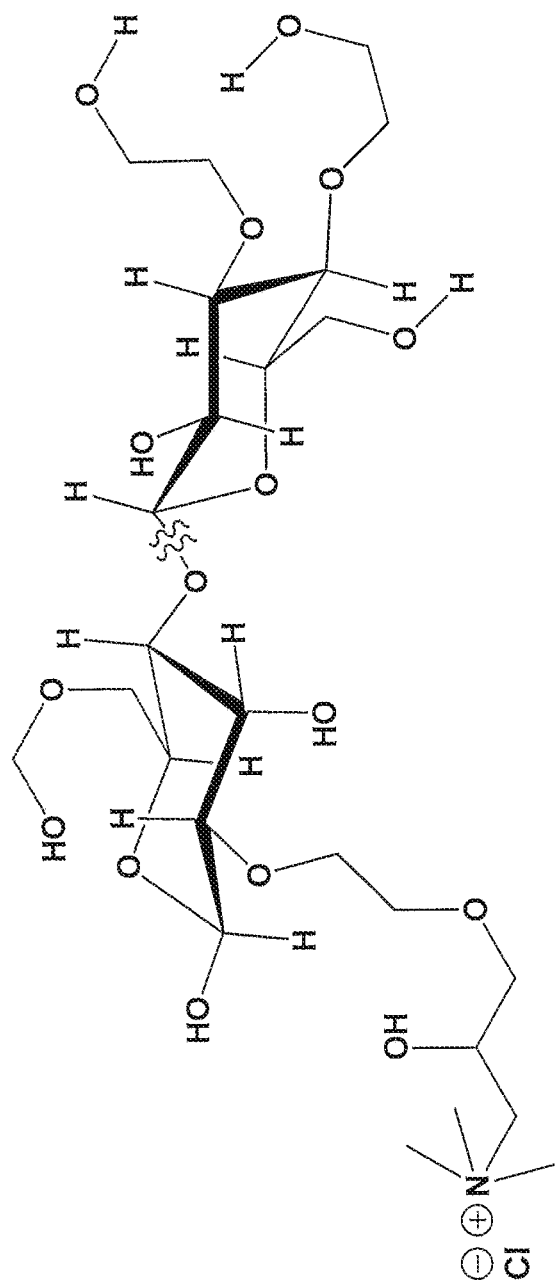
FIG. 3 schematically illustrates Polyquarternium-10 in accordance with certain embodiments described herein.

Embodiments of the present disclosure are directed to cleaning compositions with cationic surfactants. In certain embodiments, a cleaning composition is provided for cleaning textiles and clothes. Certain other embodiments provide compositions to be used as a pet shampoo or compositions to be used as a salon formula. The compositions in accordance with certain embodiments described herein can be formulated to be used at room temperature and to provide multiple benefits such as fabric-softening, antistatic and/or deodorizing properties. The compositions in accordance with certain embodiments described herein can be formulated using natural ingredients and/or ingredients for which the GRAS (generally recognized as safe) designation applies.

Hereinafter, specific embodiments of the present disclosure will now be described in more detail. The embodiments may, however, be represented in many different forms and should not be construed as being limited to the specific embodiments set forth herein. Rather, these specific embodiments are provided so that this disclosure will be thorough and complete, and will fully convey the scope of the embodiments to those skilled in the art.

Certain embodiments described herein advantageously bring together several disparate materials that have not previously been brought together to form cleaning products (e.g., shampoo; laundry cleaning product) that have striking and unique properties. Certain embodiments described herein utilize ingredients (e.g., surfactants) that are sourced from natural, edible plants (e.g., coconuts; soybeans; cellulose) and are processed using semisynthesis.

Certain embodiments described herein advantageously provide a personal care product (e.g. shampoo) that provides enhanced performance as compared with conventional products. The hair fiber, natural and isolated from outside influences such as triboelectric effects, presents a negative electrostatic charge. Conventional shampoos are reliant on anionic surfactants, under the mistaken view that the most effective shampoos are those that contain high lather synthetic anionic surfactants and that such anionic shampoo systems provide a more desirable level of cleaning and/or foaming than do shampoo systems that incorporate cationic materials or surfactants utilizing nonionic, amphoteric, or cationic cosurfactants as shampooing agents (see, e.g., U.S. Pat. No. 5,344,643). However, the conventional technology calls for water soluble, anionic carboxylic polymers to be adsorbed onto the negatively electrostatically charged hair surface, which violates the nature of electrostatic force interactions since the negatively charged anionic surfactants are repelled by the negatively charged hair surface.

Certain embodiments described herein overcome the failings of the conventional technology by specifying the robust cleaning action of the aliphatic amine oxides (e.g., cocamine oxide) by utilizing at least one cationic surfactant (e.g., polyquaternium-10) with compatible, superior and novel antiredeposition action, and which, unlike the conventional industry standard of anionic sodium carboxymethylcellulose, advantageously provides a positive electrostatic charge to attract and capture the negatively charged dirt and soil particles.

Certain embodiments described herein advantageously include various other compounds, including but not limited to one or more of the following:

Hydroxyethylcellulose: a nonionic ingredient that functions as a stabilizer, suspending agent and a formula viscosity building agent;

Cetyl hydroxyethylcellulose: a nonionic ingredient functioning both as a gentle cleansing agent and formula viscosity building agent;

Diammonium EDTA: a metal chelator designed to specifically function in an acid environment and to counteract the effects of hard water by forming complexes with and inactivating calcium, magnesium and iron ions, allowing for better foaming and cleaning performance and preventing them from being deposited onto the hair, scalp and skin;

Benzethonium chloride: a cationic ingredient that functions as an antimicrobial agent, preservative, deodorant agent, suspending agent and a cleansing agent;

Cocamidopropyl hydroxysultaine: an amphoteric ingredient that functions both as a cleansing agent and foam booster;

Soyethyl morpholinium ethosulfate: a cationic ingredient that functions as an antimicrobial agent, preservative, deodorant agent and cleansing agent;

Cocamine oxide: an amphoteric ingredient that functions as a cleansing agent, hair conditioning agent, foam booster and hydrotrope; in some formulations (e.g., formulations with pH about 4.0-6.0), Cocamine oxide can be classified as a cationic surfactant, while in other formulations (e.g., formulations with pH about 6.0-7.0), Cocamine oxide can be classified as a nonionic surfactant.

Allantoin: a botanical extract of the comfrey plant that functions as a soothing, anti-irritant, skin conditioning, moisturizing and protecting agent that increases the smoothness of the skin;

Polyquaternium-10: a cationic ingredient that functions as a novel, superior antiredeposition and suspending agent for dirt and soil, a formula viscosity building agent, an emollient and an antistatic, conditioning and moisturizing agent;

Lauryl glucoside: a nonionic ingredient that functions as a mild and gentle cleansing agent;

Maltooligosyl glucoside: a nonionic, multifunctional natural vegetable carbohydrate syrup that functions as an anti-irritant, skin conditioning and hydrating agent for sensitive skin as well as a mild and gentle cleansing agent providing luxurious foams;

Guar hydroxypropyltrimonium chloride: a cationic ingredient that functions as a conditioning agent for skin and hair, provides antistatic properties and is a formula viscosity building agent;

D-Panthenol: a form of vitamin B5 that is a moisturizer (e.g., easily penetrating the skin, sealing in hydration by boosting the skin barrier), a conditioning agent for skin and hair, rejuvenates and revitalizes skin cells and provides antistatic properties;

Polyquaternium-70: a cationic ingredient that functions to provide hair conditioning benefits, shine retention, detangling and frizz control by reducing the effects of humidity;

Behentrimonium methosulfate: a cationic ingredient that functions to provide hair conditioning benefits, provides antistatic properties, detangling, shine retention, ease of combing and improved elasticity without causing buildup on the hair and is an extremely mild cleanser;

Acetamide monoethanolamine (e.g., Acetamide MEA): functions as a conditioning agent for skin and hair, is a humectant, a foam booster, provides antistatic properties, increases sheen and the ease of wet-combing and is a formula viscosity building agent;

Acetamidopropyl trimonium chloride: a cationic ingredient that functions to provide excellent static control and a humectant designed to maintain the hairs' critical moisture balance;

Hexylene glycol: a cosolvent, coupling agent and cleanser;

Coco-glucoside and glycol distearate: two components of a pearlizing formula in accordance with certain embodiments described herein.

Certain embodiments described herein advantageously provides a cleaning product having a formula in which none or substantially none of its constituent hydrocarbon entities are anions. For example, all of the hydrocarbon species of the cleaning product in accordance with certain embodiments described herein, if they are ions, are either cations or amphoteric ions, or they are nonionic hydrocarbon species or amphoteric substances, and they are all robustly compatible. In certain embodiments, the hydrocarbon species of the cleaning product function independently and synergistically, in an unfettered manner, and many (e.g., most; almost all) of the ingredients are multifunctional.

In some embodiments, a cleaning composition comprises water, at least one cationic surfactant and at least one nonionic surfactant. In certain such embodiments, the at least one cationic surfactant comprises at least one cationic surfactant (e.g., at least two cationic surfactants; at least three cationic surfactants; at least four cationic surfactants; more than four cationic surfactants) selected from the group consisting of: Polyquaternium-1, Polyquaternium-4, Polyquaternium-6, Polyquaternium-10, Polyquaternium-11, Polyquaternium-12, Polyquaternium-15, Polyquaternium-16, Polyquaternium-18, Polyquaternium-20, Polyquaternium-30, Polyquaternium-43, Polyquaternium-51, Polyquaternium-57, Polyquaternium-67, Polyquaternium-22, Polyquaternium-37, Polyquaternium-44, Polyquaternium-52, Polyquaternium-59, Polyquaternium-68, Polyquaternium-24, Polyquaternium-38, Polyquaternium-46, Polyquaternium-53, Polyquaternium-64, Polyquaternium-69, Polyquaternium-28, Polyquaternium-39, Polyquaternium-47, Polyquaternium-55, Polyquaternium-65, Polyquaternium-70, Polyquaternium-72, Polyquaternium-73, Polyquaternium-76, Polyquaternium-80, Quaternium-15, Quaternium-26, Quaternium-33, Quaternium-70, Quaternium-75, Quaternium-79, Quaternium-82, Quaternium-83, Quaternium-84, Quaternium-89, Quaternium-90, Quaternium-91, Quaternium-95, Benzethonium chloride, Quaternium-Λ (a,a'-[[methyl[3-(tridecyloxy)propyl]iminio]di-2,1-ethanediyl]bis][w-hydroxy-poly(oxy-1,2-ethanediyl)] chloride), Benzalkonium chloride, behentrimonium methosulfate, behentrimonium chloride, acetamidopropyltrimonium chloride, guar hydroxypropyltrimonium chloride, soyethyl morpholinium ethosulfate (also known as Quaternium-2) and cocamine oxide. In certain embodiments, the at least one nonionic surfactant is selected from the group consisting of: cetyl hydroxyethylcellulose, cocamidopropyl hydroxysultaine, lauryl hydroxysultaine, coconut fatty alcohol polyglycol ethers with ethylene oxide (EO) units ranging between 2 and 30, C8-C22 alkyl glucosides, for example decyl glucoside, lauryl glucoside, coco glucoside and maltooligosyl glucoside; C8-C16 alkyl polyglucosides for example oligomeric D-glucopyranose and C8-C16 alkyl glycosides, C8-C22 alkyl maltosides, for example n-dodecyl-β-D-maltopyranoside (DDM), cocamide MIPA and cocamide DIPA.

In certain such embodiments, the at least one cationic surfactant comprises from 1 wt. % to 20 wt. % of the total weight of the composition. In some embodiments, the at least one cationic surfactant comprises from 1 wt. % to 10 wt. % of the total weight of the composition. In some embodiments, the at least one cationic surfactant comprises from 10 wt. % to 15 wt. % of the total weight of the composition. In certain embodiments, the composition contains substantially no anionic surfactants (e.g., an anionic surfactant component of the composition comprises less than 1 wt. % of the total weight of the composition).

In some embodiments, the cleaning composition comprises at least one nonionic surfactant (e.g., at least two nonionic surfactants; at least three nonionic surfactants; at least four nonionic surfactants; more than four nonionic surfactants) selected from the group consisting of: cetyl hydroxyethylcellulose, cocamidopropyl hydroxysultaine, lauryl hydroxysultaine, cocamine oxide, coconut fatty alcohol polyglycol ethers with ethylene oxide (BO) units ranging between 2 and 30, C8-C22 alkyl glucosides, for example decyl glucoside, lauryl glucoside, coco glucoside and maltooligosyl glucoside; C8-C16 alkyl polyglucosides for example oligomeric D-glucopyranose and C8-C16 alkyl glycosides, C8-C22 alkyl maltosides, for example n-dodecyl-β-D-maltopyranoside (DDM), cocamide MIPA (Cocamide Monoisopropanolamide) and cocamide DIPA (Cocamide Diisopropanolamide).

In certain such embodiments, the at least one nonionic surfactant comprises less than or equal to 5 wt. % of the total weight of the composition, less than or equal to 2 wt. % of the total weight of the composition and/or less than or equal to 1 wt. % of the total weight of the composition.

In some embodiments, the cleaning composition comprises at least one thickening agent selected from the group consisting of: hydroxyethylcellulose and cetyl hydroxyethylcellulose.

In certain such embodiments, the at least one thickening agent comprises less than or equal to 5 wt. % of the total weight of the composition, less than or equal to 3 wt. % of the total weight of the composition and/or less than or equal to 1 wt. % of the total weight of the composition.

In some embodiments, the cleaning composition comprises at least one foaming agent selected from the group consisting of: cocamidopropyl hydroxysultaine, lauryl hydroxysultaine, cocamine oxide, coconut fatty alcohol polyglycol ethers with ethylene oxide (BO) units ranging between 2 and 30, C8-C22 alkyl glucosides, for example decyl glucoside, lauryl glucoside, coco glucoside, maltooligosyl glucoside; C8-C16 alkyl polyglucosides for example oligomeric D-glucopyranose and C8-C16 alkyl glycosides, C8-C22 alkyl maltosides, for example n-Dodecyl-β-D-maltopyranoside (DDM), cocamide MIPA and cocamide DIPA.

In certain such embodiments, the at least one foaming agent comprises from 1 wt, % to 20 wt. % of the total weight of the composition, from 1 wt. % to 10 wt. % of the total weight of the composition and/or from 10 wt. % to 15 wt. % of the total weight of the composition.

In some embodiments, the cleaning composition comprises at least one skin conditioner, e.g., allantoin.

In certain such embodiments, the at least one skin conditioner comprises less than or equal to 5 wt. % of the total weight of the composition, less than or equal to 3 wt. % of the total weight of the composition and/or less than or equal to 1 wt. % of the total weight of the composition.

In some embodiments, the cleaning composition comprises at least one fragrance agent selected from the group consisting of: amyl acetate, isoamyl acetate and hexyl acetate.

In certain such embodiments, the at least one fragrance agent comprises less than or equal to 5 wt. % of the total weight of the composition, less than or equal to 3 wt. % of the total weight of the composition and/or less than or equal to 1 wt. % of the total weight of the composition.

In some embodiments, the cleaning composition comprises at least one deodorizing agent, e.g., soyethyl morpholinium ethosulfate.

In certain such embodiments, the at least one deodorizing agent comprises less than or equal to 5 wt, % of the total weight of the composition, less than or equal to 3 wt. % of the total weight of the composition and/or less than or equal to 1 wt. % of the total weight of the composition.

In some embodiments, the cleaning composition comprises at least one chelating agent selected from the group consisting of: diammonium EDTA, disodium EDTA, tetrasodium EDTA, ethylenediamine-N,N'-disuccinic acid (EDDS), citric acid, methyiglycinediacetic acid (synonym: α-alaninediacetic acid) and N,N-bis(carboxymethyl)-L-glutamic acid (GLDA) (e.g., L-glutamic acid N,N' diacetic acid).

In certain such embodiments, the at least one chelating agent comprises less than or equal to 5 wt. % of the total weight of the composition, less than or equal to 3 wt. % of the total weight of the composition and/or less than or equal to 1 wt. % of the total weight of the composition.

In some embodiments, the cleaning composition comprises water (e.g., as a solvent) and the water is from 60 wt. % to 90 wt. % of the total weight of the composition.

In certain such embodiments in which the water is a solvent, the composition comprises at least one co-solvent selected from the group consisting of: hexylene glycol, ethanol and 1-propanol.

In certain such embodiments, the at least one co-solvent comprises from 1 wt. % to 10 wt. % of the total weight of the composition, from 1 wt. % to 5 wt. % of the total weight of the composition and/or from 5 wt. % to 10 wt. % of the total weight of the composition.

In some embodiments, the at least one cationic surfactant comprises benzethonium chloride, Quaternium-Λ and Polyquaternium-10 or Polyquaternium-1. FIG. 3 schematically illustrates Polyquaternium-10 in accordance with certain embodiments described herein. In some embodiments, wherein the cleaning composition comprises at least one nonionic surfactant, the at least one nonionic surfactant comprise cocamine oxide and cocamidopropyl hydroxysultaine.

In some embodiments, wherein the cleaning composition comprises at least one thickening agent, the at least one thickening agent comprises hydroxyethylcellulose and cetyl hydroxyethylcellulose. In some embodiments, wherein the cleaning composition comprises at least one foaming agent, the at least one foaming agent comprises cocamidopropyl hydroxysultaine and cocamine oxide. In some embodiments, wherein the cleaning composition comprises at least one deodorizer, the at least one deodorizer comprises soyethyl morpholinium ethosulfate. In some embodiments, wherein the cleaning composition comprises at least one skin conditioner, the at least one skin conditioner comprises allantoin.

In some embodiments, wherein the cleaning composition comprises at least one fragrance agent, the at least one fragrance agent comprises amyl acetate, isoamyl acetate and hexyl acetate. In some embodiments, wherein the cleaning composition comprises at least one chelating agent, the at least one chelating agent comprises diammonium EDTA. In some embodiments, wherein the cleaning composition comprises at least one co-solvent, the at least one co-solvent comprises hexylene glycol.

In some embodiments, the cleaning composition has a pH in the range of 1 to 7. In some embodiments, the cleaning composition has a pH in the range of 4 to 7. In some embodiments, the cleaning composition comprises micelles with particle size in the range of 20 Å and 200 Å. In some embodiments, the cleaning composition comprises micelles with particle size in the range of 20 Å and 50 Å. In some embodiments, the cleaning composition comprises micelles with particle size in the range of 50 Å and 75 Å. In some embodiments, the cleaning composition comprises micelles with particle size in the range of 75 Å and 125 Å. In some embodiments, the cleaning composition comprises a plurality of micelles configured to be electrostatically attracted and bound to dirt particles having an opposite charge so as to substantially surround the dirt particles (e.g., having particle sizes greater than 0.2 micron; greater than 0.5 micron; greater than 1 micron). In this way, the dirt particles can be solubilized in a manner that contrasts with conventional cleaning components having micelles with the same charge as the dirt particles.

Certain embodiments described herein advantageously do not include alkaline compounds. In this way, certain such embodiments provide a laundry cleaning composition that can be added to the wash cycle of a clothes washer, and can avoid stripping off a surface layer from the fabrics, thereby keeping the fabrics soft and avoiding added rigidity. By utilizing cationic surfactants, certain embodiments described herein advantageously provide anti-static properties by avoiding buildup of charge. Thus, certain embodiments described herein advantageously reduce the need for additional water softening or conditioning agents and/or anti-static agents (e.g., cloths or dryer sheets) added to the clothes in the clothes dryer.

Certain embodiments described herein advantageously provide laundry cleaning compositions that are used with water at room temperature. Certain embodiments described herein advantageously provide laundry cleaning compositions that can be used with fabrics that are labeled as "dry clean only," Certain embodiments described herein are advantageously provide laundry cleaning compositions that avoid, reduce, or remove dinginess of fabrics that has resulted from previous conventional cleanings of these fabrics.

Certain embodiments described herein advantageously provide body wash compositions. Certain embodiments described herein advantageously provide a unique, unprecedented and even revolutionary four-in-one hair care product that can be used as a shampoo, conditioner, detangler and frizz eliminator, all at once. Certain embodiments described herein advantageously provide a product that can be used as an animal shampoo.

Certain embodiments described herein advantageously consist essentially of ingredients which are "generally recognized as safe" ("GRAS"), For example, the surfactants of certain embodiments described herein have parent, precursory compounds that are found in plant sources (e.g., coconuts, soybeans, cellulose, etc.), These components can be from edible plant sources (e.g., a natural biomolecule) but are not able to be used "as is" as a product ingredient to perform a surfactant function. To become useful as a surfactant in a cleaning composition, the biomolecule is to be transformed (e.g., by semisynthesis).

With any chemical synthesis, including semisynthesis, there are two sources of concern for purity with the finished product. First, there can be impurities due to the presence of unreacted starting materials (e.g., chemical syntheses that does not reach 100% completion; chemical syntheses that are less than perfect). Second, there can be side reaction by-products. In both cases, a costly (and less than perfect) separation process is generally then employed to try to isolate the desired main product from the reaction mixture. The entrained, unreacted starting materials and side reaction by-products are impurities in the desired end product. Depending on what they are, these by-products can range from innocuous to toxic, and toxic is of considerable concern, Collectively, whether trace amounts of unreacted starting materials or side reaction by-products, the designation "toxic tagalongs" is used herein, for such non-innocuous impurities that would compromise the desired cleaning compounds.

Without being bound by theory, the following discussion provides some insights into the performance of certain embodiments described herein. Unless defined otherwise, all technical and scientific terms used herein have their broadest reasonable meaning, including but not limited to the same meaning as is commonly understood by one of ordinary skill in the art to which this disclosure belongs. In the event that there is a plurality of definitions for a term herein, those in this section prevail unless stated otherwise.

As used herein, the term "surfactant" refers to a "surface active agent" as is generally accepted in the art. As the phrase "surface active agent" implies, the molecule possesses surface activity, a property associated with the chemical structure of the molecule. Surfactants are compounds that lower the surface tension (or interfacial tension) between two liquids, between a gas and a liquid, or between a liquid and a solid. Surfactants may act as detergents, wetting agents, emulsifiers, foaming agents and dispersants. Surfactants are usually organic compounds that are amphiphilic, meaning they contain both hydrophobic groups (their tails) and hydrophilic groups (their heads). Surfactants are molecules that give ions which are essentially hydrocarbons, modified by a charged group at one of its two ends, which are each attached to the molecule by a covalent bond, and have diametrically opposite polarities—a polar end and a non-polar end. The non-polar end is lyophilic (e.g., strongly attracted to organic molecules) while the strongly polar end is lyophobic (e.g., having little attraction for organic molecules) and strongly hydrophilic (e.g., attracted to polar groups, such as water). This dual polarity causes the molecule to align itself with respect to the polar nature of the surfaces with which it may come into contact.

For example, when surfactant monomers are placed in water, they form aggregates, such as micelles, where the hydrocarbon (hydrophobic) tails form the core because hydrocarbons are insoluble in polar solvents and the hydrophilic heads are in contact with the water molecules. The charges at the surface of the micelle are dissolved in water, and the hydrocarbon chains in the interior are dissolved in each other. X-ray studies of surfactant suspensions show that at low concentrations, the micelles are approximately spherical with a particle size (diameter) of about 50 Å. The cleansing action of surfactants is thought to stem from the dissolving of grease (essentially hydrocarbon in nature) in these hydrocarbon interior clusters.

As used herein, the term "anionic surfactant" has its broadest reasonable interpretation, including referring to long-chain ion molecules where the part containing the hydrophobic group carries a negative electric charge. The hydrophilic moieties of anionic surfactants can be based on carboxylic, sulfuric, sulfonic and phosphoric acids, but are not limited thereto. Anionic surfactants are usually neutral pH molecules, the acids having been converted to their corresponding alkali salt. Solubility can be related to (e.g., dependent on) the length of the alkyl chain. FIG. 1 shows a listing of some example anionic surfactants in accordance with certain embodiments described herein.

As used herein, the term "cationic surfactant" has its broadest reasonable interpretation, including referring to long-chain molecules wherein the part containing the hydrophobic group carries a positive electric charge and are typified by the quaternary ammonium salts of saturated fatty acid amines. A typical ion is —$N(CH_3)_3^+$, the quaternary ammonium ion. Counter ions include but are not limited to: chloride, methosulfate, or ethosulfate. The cationic surfactants can be used as emulsifying agents, fabric softeners, hair conditioning agents, dyeing agents, agents with outstanding germicidal activity and as described herein, can be used for detergent applications.

As used herein, the term "nonionic surfactant" has its broadest reasonable interpretation, including referring to molecules having a hydrophilic head group and a hydrophobic tail, that carry no charge and are relatively non-toxic (e.g., amphoteric surfactants; zwitterionic surfactants). The hydrophobic moiety of the nonionic surfactant may be, for example, alkyl, fluoroalkyl, alkaryl or steroidal in nature. Various types of nonionic surfactants, such as polyglycerol alkyl ethers, glucosyl dialkyl ethers, crown ethers, ester-linked surfactants, polyoxyethylene alkyl ethers, sorbitan esters (e.g., Spans), polysorbates (e.g., Tweens), sorbitol-based nonionic surfactants, sorbitan-based nonionic surfactants, Polysorbate-20, Polysorbate-60, Polysorbate-61 and PEG-80 sorbitan laurate, used for the preparation of nonionic surfactants that fall into the GRAS category and are mild to use. Another class of nonionic surfactants comprises amine oxides (e.g., lauryldimethylamine oxide, which can be a foaming agent). FIG. 2 shows a listing of some example nonionic surfactants in accordance with certain embodiments described herein.

Many nonionic surfactants are based on the reaction of ethylene oxide with certain hydrophobes (e.g., water-insoluble, lyophilic molecules that are converted into surfactants by appropriate reactions). Molecules containing active hydrogens will react with ethylene oxide (EO) to form polyethylene glycol derivatives. For example, hydroxyls, carboxyls, amines and mercaptyl groups are active hydrogen types that can be ethoxylated. The water solubility of ethoxylated compounds is a function of hydrogen-bond formation between water molecules with ether oxygens. With an ether, where two carbon atoms flank a more electronegative oxygen atom, this group is named a hydrogen bond acceptor, or proton acceptor. Therefore, the greater the number of ether groups, the greater the number of hydrogen-bonding sites for solubilizing the compound. As the number of moles of ethylene oxide increases for a given hydrophobe, the solubility of the compound increases.

As used herein, the term "Cloud Point" has its broadest reasonable interpretation, including referring to the temperature at which a one percent solution of a nonionic surfactant forms a cloud of insolubility. Cloud point is influenced by the structure of the hydrophobe and the degree of ethoxylation. Temperature also has an influence on hydrogen bonds, such that as the temperature increases, H-bonds rupture. At some elevated temperature, enough of them will have broken to cause a cloud of insolubility to form. Eventually the surfactant will separate into an insoluble layer floating on water.

Cloud point of a given hydrophobe is influenced by the number of ether units available to hydrogen-bond with water. As an example, for a particular hydrophobe, if eight moles of ethylene oxide (EO) result in a molecule that is barely soluble at room temperature, increasing the EO content to 16 will result in the new product being soluble up to the boil. This concept can be useful for designing surfactants that provide a desired performance at given temperatures.

Another property of surfactants is the hydrophilic/lyophilic balance ("HLB") which can be a function of choosing the desired fatty alkyl group. It is desirable that a molecule have a balance of water and oil solubility for the molecule to function as a surfactant. For example, the molecule is preferably not too water soluble, otherwise it will not form micelles, yet at the same time it is preferably sufficiently soluble to do its job as a surfactant. The solubility of a surfactant-molecule-in-water-verses-oil depends on the water solubilizing group.

For example, nonylphenol, which can be considered as a hydrophobe, is very slightly soluble in water and is highly soluble in oils (e.g., organic solvents). If one mole of ethylene oxide (EO) is added, the water solubility is increased slightly while oil solubility is decreased. As more EO is added, water solubility continues to increase at the expense of oil solubility. When five to nine moles of EO have been added, the molecule is equally soluble in water and in oil. Above nine moles of EO, the water solubility continues to increase at the expense of oil solubility. Picturing the HLB concept as a balance, with one side representing oil solubility while the other side represents water solubility, for the ethoxylated nonylphenol, there is a solubility balance of the ethoxylate between the two solvents. The lower ethoxylates are more soluble in oil than in water, where the converse is true of the higher ethoxylates, which become more water soluble and less oil soluble. This balance of solubility can be utilized for any given ethoxylate to perform as a surfactant. For example, for the molecule to affect an interface, it is desirable that the molecule evenly distribute itself between the two phases without being preferentially attracted to either phase.

When surfactant molecules are added to pure water one molecule at a time, the first few molecules, called surfactant monomers, align at the air/water interface and the hydrocarbon tails orient toward air. The driving force for this alignment is the non-polar tails seeking to associate themselves with the most non-polar interface they can find, in this case air. These surfactant monomers are surrounded by water molecules that create a "cage" or solvation shell connected by hydrogen bonds. This water cage is similar to a clathrate and has an ice-like crystal structure. As additional molecules are added, they too will align at the water/air interface until all of the surface area is completely packed.

As more molecules are added, they are forced into the bulk of the water, floating about as individual, solvent-caged molecules (called monomers) until a saturation level is reached. At this point, called the critical micelle concentration (CMC), surfactant monomers agglomerate into water soluble clumps which are called micelles, where the lyophobic tails are associated with themselves and the hydrophilic heads are surrounded by water molecules. Micelles thus present a molecular assembly, in which the individual components are thermodynamically in equilibrium with the surfactant monomers in the surrounding medium.

Surface tension can be defined as the interfacial tension between a liquid and its vapor. One of the methods of measuring surface tensions involves using a du Noy tensiometer. This technique measures the force necessary to pull a platinum ring away from a liquid. For pure water, the force is 72 dynes/cm.

A plot of surfactant concentration verses water surface tension shows that it takes very little surfactant to quickly lower the surface tension. At a certain low concentration, the plot levels off and maintains the low surface tension value regardless of how much more surfactant is added. The concentration where the curve levels off is called the critical micelle concentration (CMC). For example, CMC is the minimum concentration of soap that forms micelles. Increasing the soap concentration beyond this point simply increases the number of micelles in the solution.

Ionic surfactants are different than nonionic polyethers. Like most water-soluble materials, ionic surfactants are more soluble in hot water than in cold. Since more molecules are individually solvated, it follows that a greater amount of surfactant will be needed to reach the critical micelle concentration. Therefore, for ionic surfactants, CMC increases with increasing temperature and the number of available micelles is reduced.

Nonionic surfactants are less soluble in hot water than in cold, and more micelles are formed as the temperature is raised. This unique feature gives rise to the fact that nonionic surfactants are most effective at temperatures just below their cloud point. At low temperatures, their solubility is higher so a greater number of molecules are needed to reach the critical micelle concentration.

As used herein, the term "Electrostatic Force" has its broadest reasonable interpretation, including referring to electric force that acts between charged particles (positively and negatively charged particles). The interaction is attractive if the charges are opposite. The interaction is repulsive if the charges are similar.

In certain embodiments, a typical garment fiber, for example, is made of cellulose, and each cellulose macromolecule contains a plurality of pendant hydroxymethyl (alcohol) substituents, of which many oxidize in situ to a corresponding plurality of covalently bonded carboxylic acid functionalities. When in water, these fibers, which now present a high density of these carboxylic acid functionalities, develop a negative surface charge, setting up an electric field which attracts positively charged species. Further, predominantly because of the phenomenon of isomorphic substitution, soil particles typically present a negative electrostatic charge. In view of the negative electrostatic charge fields presented by both garment fibers and soil, certain embodiments described herein utilize one or more cationic surfactants, or a mixture of one or more nonionic surfactants and one or more cationic surfactants as cleaning compositions.

In contrast to certain embodiments described herein, current industry standards use sodium carboxymethyl cellulose (SCMC) as an anti-redeposition agent. SCMC is an anionic surfactant and hence negatively charged, and the targeted soil particles and fabric fibers are also negatively charged (FIG. 6). Therefore, the SCMC based agents and soil particles will repel each other and will be detrimental to the agent activity.

Embodiments

Example embodiments below are for illustrative purposes only, and the scope of the disclosure is not limited to the example embodiments. FIGS. 4A-4D show various example compositions in accordance with certain embodiments described herein. In certain embodiments described herein, one or more of the components are multifunctional. Certain other example embodiments add natural color to the compositions listed in FIGS. 4A-4D.

In some embodiments, hydroxyethylcellulose is used as a nonionic, water soluble polymer for product rheology control.

In some embodiments, cetyl hydroxyethylcellulose is used as a nonionic, water soluble polymer functioning as a cleaner, soil suspending agent and for product rheology control. Additionally it can function also to retain moisture levels on the skin (e.g., useful when customers use the cleaning composition for hand washing).

In some embodiments, diammonium EDTA provides water softening properties by chelating the hard water metal ions, for example, calcium, magnesium and iron.

In some embodiments, cocamidopropyl hydroxysultaine is used as a high foaming amphoteric surfactant derived from coconut fatty acids. It functions as a cleaner while concomitantly boosting the foaming capabilities of the cationic formula in certain embodiments (e.g., where such cationic systems are otherwise delimited by being low foaming).

In some embodiments, maltooligosyl glucoside is a natural carbohydrate syrup that is used to impart a smooth texture and long-lasting foam to personal care products. A glycerin alternative, maltooligosyl glucoside is used in some embodiments to protect skin against irritation, e.g., in products formulated for sensitive skin. In some embodiments, maltooligosyl glucoside is used to provide texture, resulting in a fine and rich lather for cleansing products and a luxuriant feel in hair care products. In some embodiments, maltooligosyl glucoside is also used as a foam conditioning agent.

In some embodiments, soyethyl morpholinium ethosulfate is used as a naturally sourced deodorizer. Additionally, it can function also as a cleaner.

In some embodiments, cocamine oxide is used as a high foaming nonionic surfactant. It functions as a cleaner while concomitantly boosting the foaming capabilities of the cationic formula in certain embodiments (e.g., where such cationic systems are otherwise delimited by being low foaming).

In some embodiments, allantoin is used as a naturally occurring nitrogenous compound derived from comfrey, used as a skin conditioning agent and skin protectant (e.g., useful when customers use the cleaning composition for hand washing).

Figure 5A:
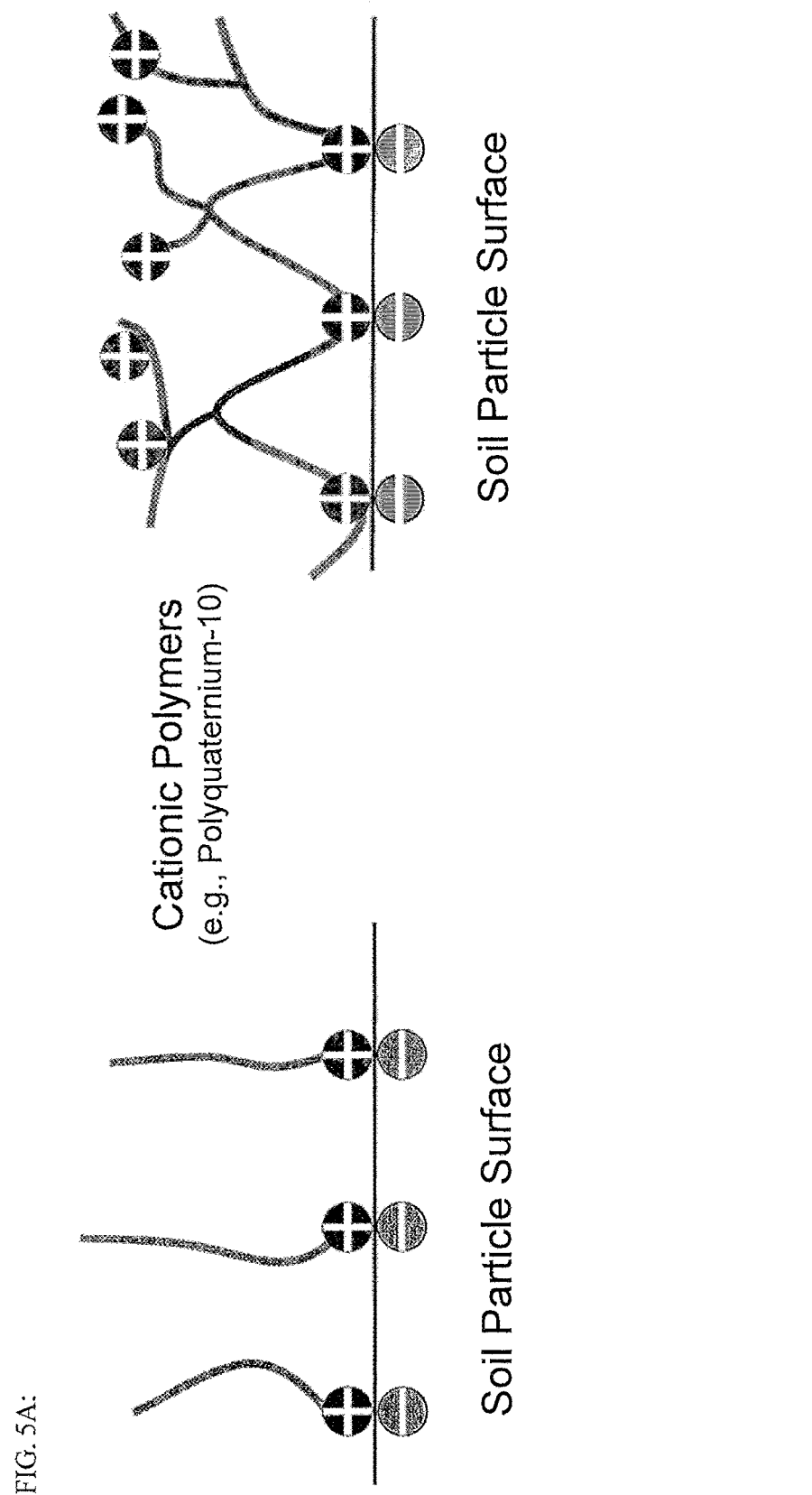
FIGS. 5A and 5B schematically show two example views of Polyquaternium-10 molecules at the surface of a soil particle in accordance with certain embodiments described herein.
Figure 5B:
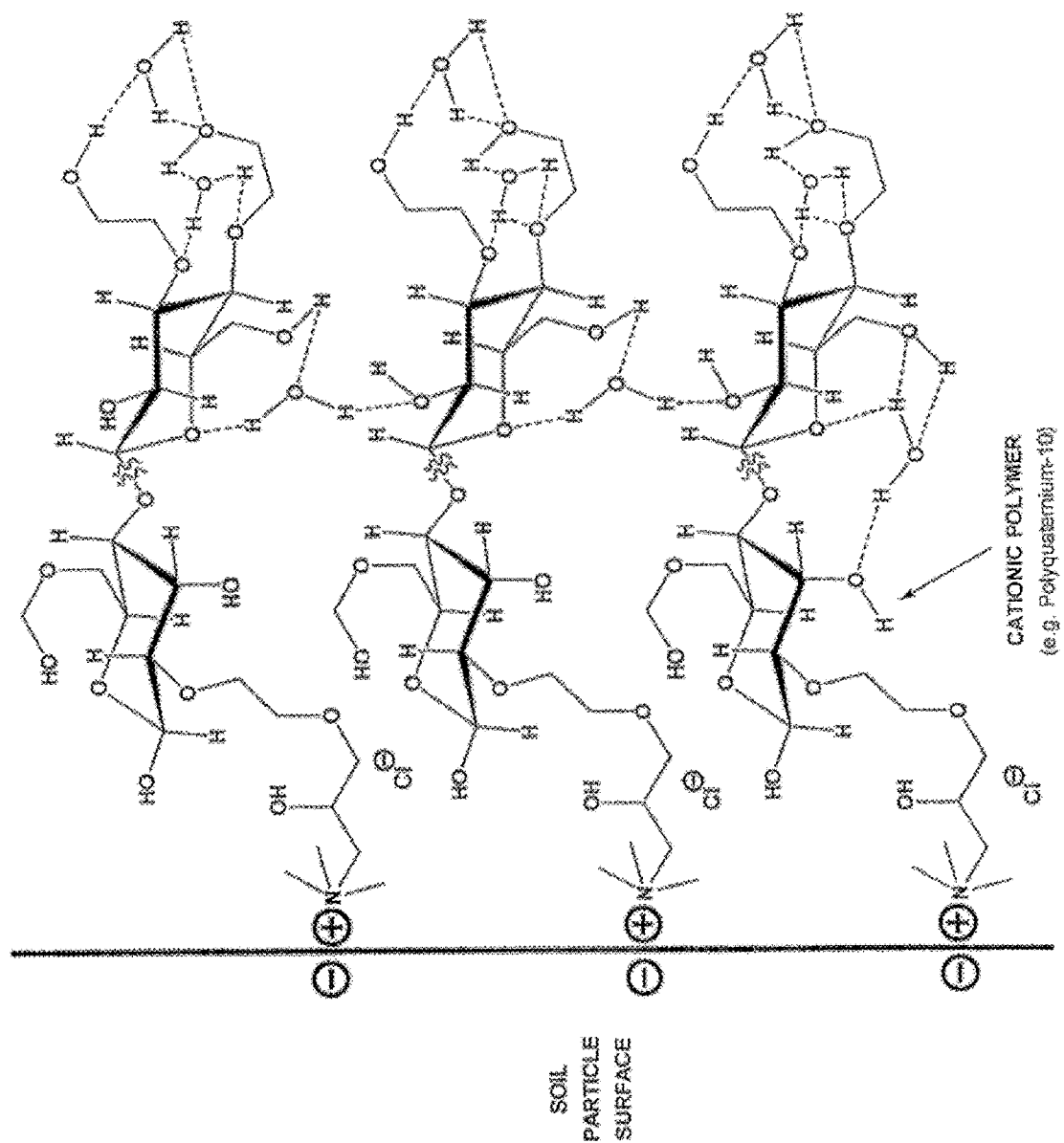
Figure 5C:
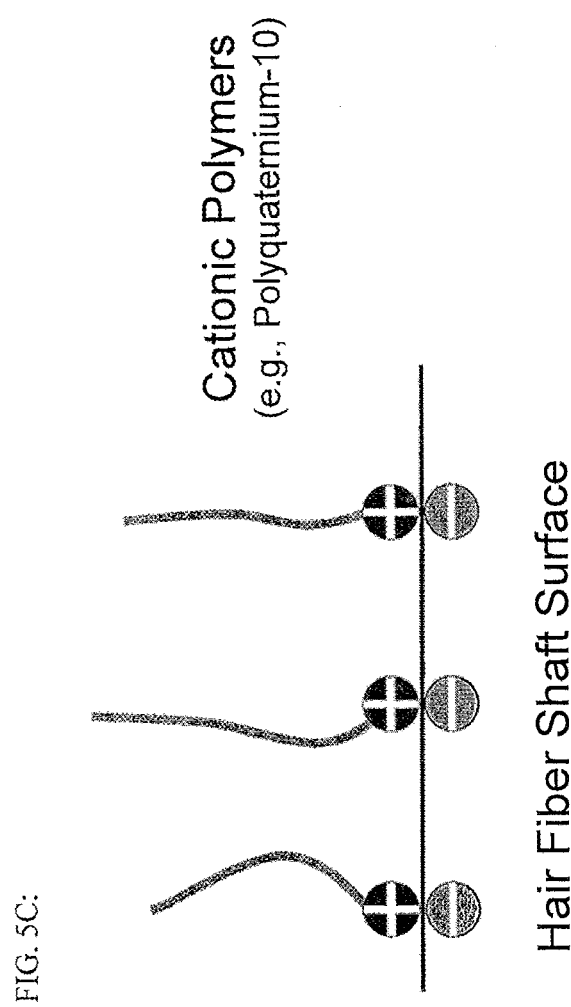
FIGS. 5C and 5D schematically show two example views of Polyquaternium-10 molecules at the surface of a hair fiber shaft in accordance with certain embodiments described herein.
Figure 5D:
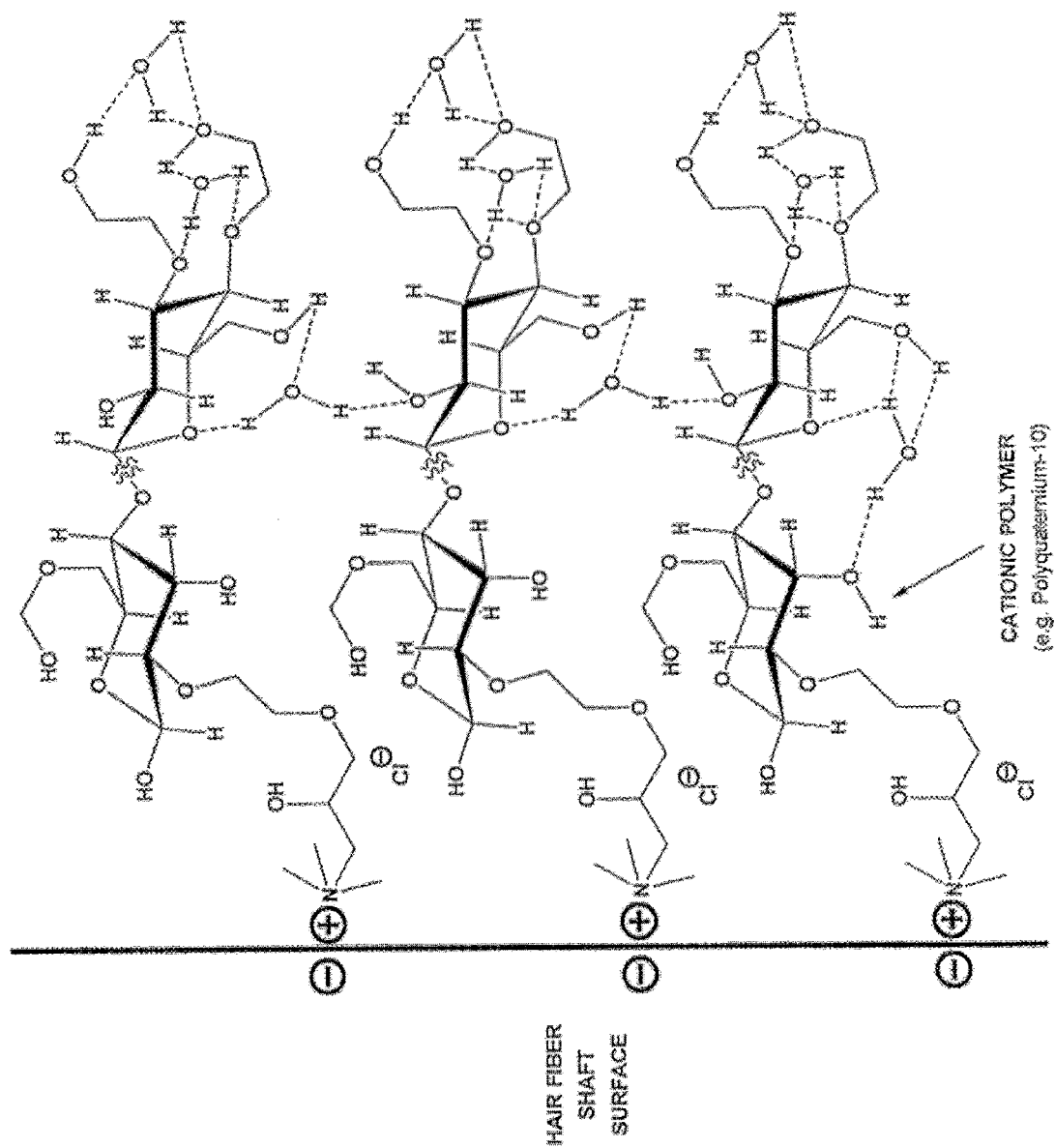
Figure 5E:
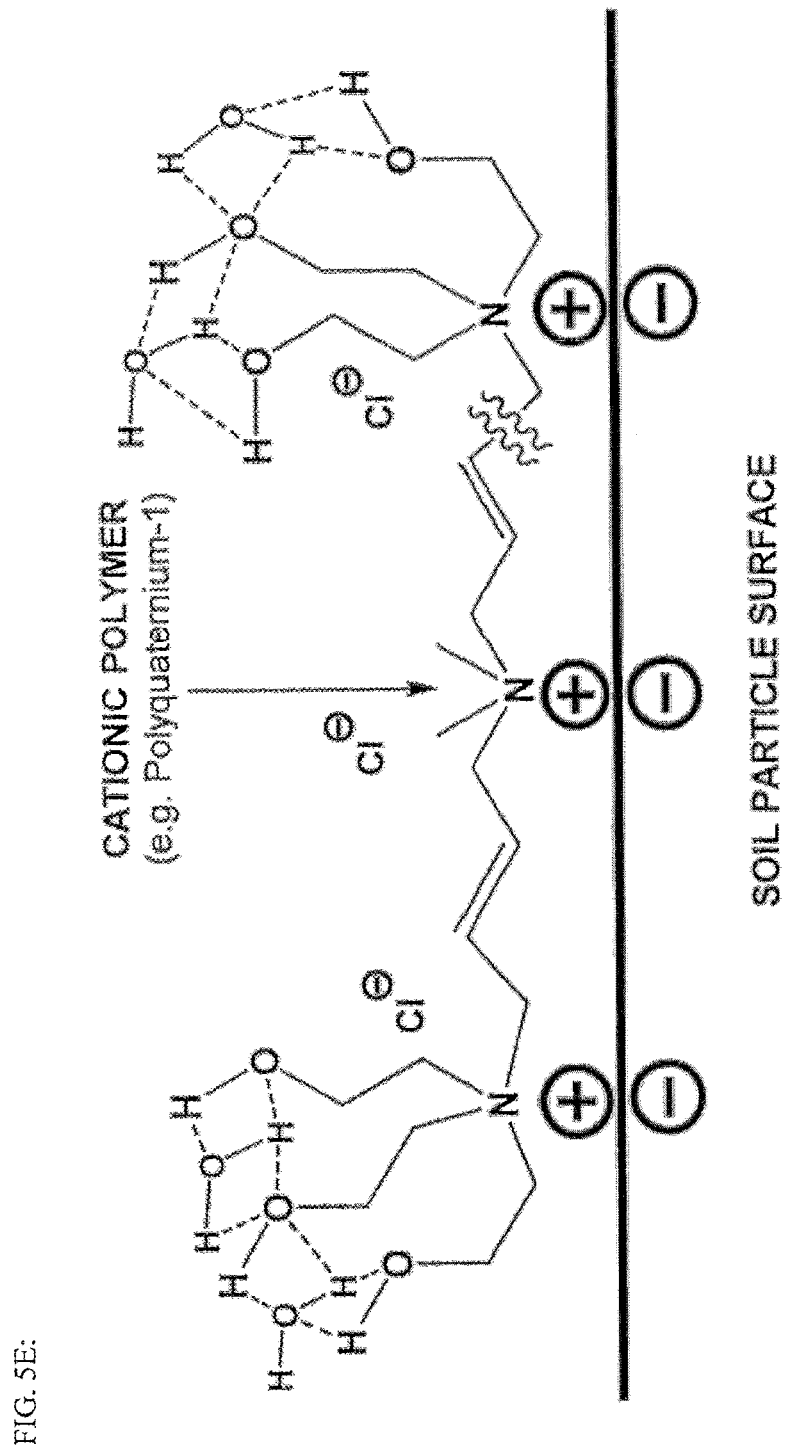
FIG. 5E schematically shows an example view of a Polyquaternium-1 molecule at the surface of a soil particle in accordance with certain embodiments described herein.
Figure 5F:
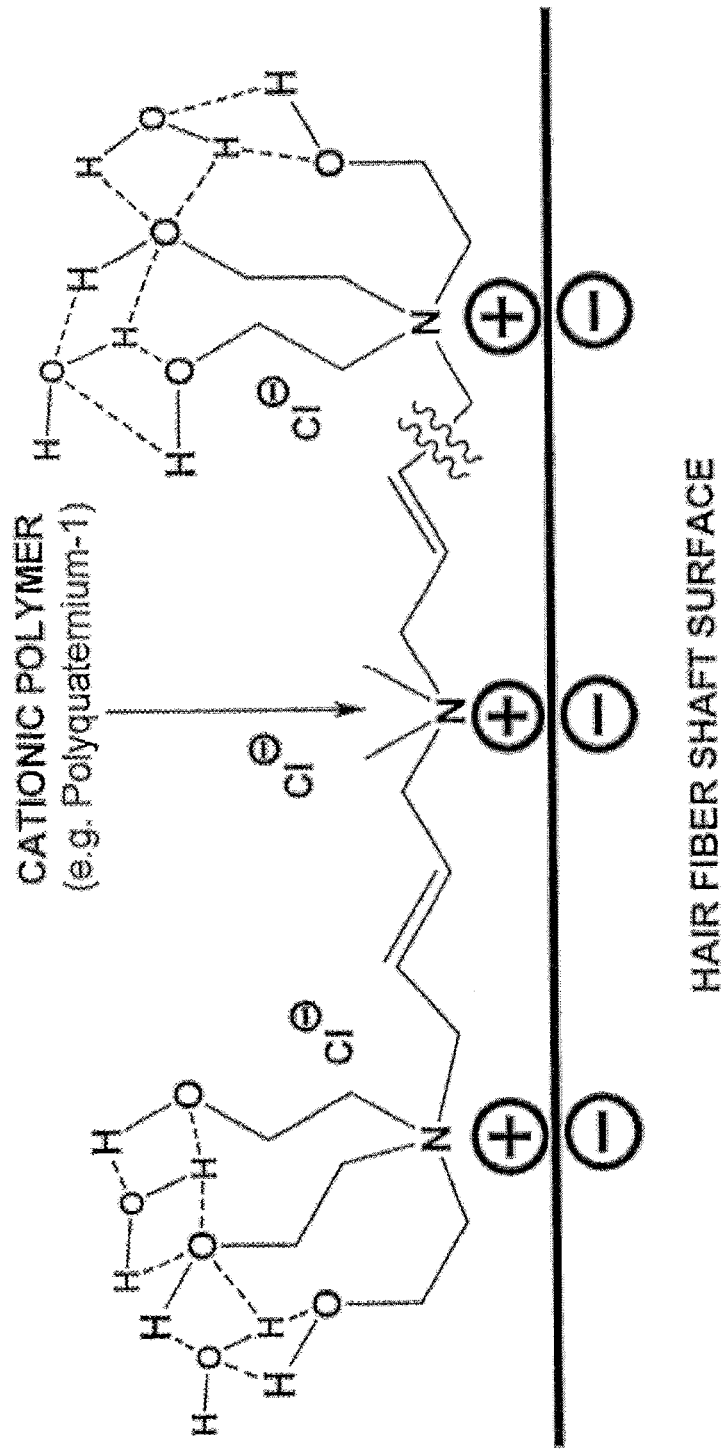
FIG. 5F schematically shows an example view of a Polyquaternium-1 molecule at the surface of a hair fiber shaft in accordance with certain embodiments described herein.

In some embodiments, Polyquaternium-10, which is a hydroxyethylcellulose, derived from naturally occurring cellulose further transformed into a water soluble, polymeric quaternary ammonium salt. Polyquaternium-10 functions as an anti-redeposition agent (e.g., since it presents a positive electrostatic charge) and also functions as a cleaner, and for product rheology control. FIGS. 5A and 5B schematically show two example views of Polyquaternium-10 molecules at the surface of a soil particle in accordance with certain embodiments described herein, and FIGS. 5C and 5D schematically show two example views of Polyquaternium-10 molecules at the surface of a hair fiber shaft in accordance with certain embodiments described herein. FIG. 5E schematically shows an example view of a Polyquaternium-1 molecule at the surface of a soil particle in accordance with certain embodiments described herein. FIG. 5F schematically shows an example view of a Polyquaternium-1 molecule at the surface of a hair fiber shaft in accordance with certain embodiments described herein.

In some embodiments, hexylene glycol, a low molecular weight, small molecule surfactant, is used as a co-solvent, coupling agent, blending agent and skin conditioner (e.g., useful when customers use the cleaning composition for hand washing).

In some embodiments, isoamyl acetate and hexyl acetate that are natural fruit esters that function as cleaners and also have the role of imparting to the cleaning composition a natural fruit scent. These compounds are volatile, and can be used to desirably evaporate away, leaving little or no scent on washed surfaces (e.g., clothes, either line or machine dried).

In some embodiments, benzethonium chloride and a,a'-[[methyl[3-(tridecyloxy)propyl]iminio]di-2,1-ethanediyl] bis][w-hydroxy-poly(oxy-1,2-ethanediyl)]chloride (also referred to as "Quaternium-Λ") are used as a cleaner.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

What is claimed is:

1. A cleaning composition comprising:
   a) water;
   b) at least two cationic ingredients selected from the group consisting of Polyquaternium-1, Polyquaternium-10, Quaternium-Λ, soyethyl morpholinium ethosulfate and cocamine oxide;
      wherein at least one of the at least two cationic ingredients is selected from the group consisting of Quaternium-Λ and soyethyl morpholinium ethosulfate; and
   c) at least two nonionic ingredients selected from the group consisting of cetyl hydroxyethylcellulose, cocamidopropyl hydroxysultaine, lauryl glucoside, maltooligosyl glucoside and hydroxyethylcellulose.

2. The composition of claim 1, wherein if an anionic component is present in the composition, it is present in an amount comprising less than 1 wt. % of the total weight of the composition.

3. The composition of claim 1, wherein the at least two nonionic ingredients comprise less than or equal to 5 wt. % of the total weight of the composition.

4. The composition of claim 1, wherein the water is from 60 wt, % to 90 wt. % of the total weight of the composition.

5. The composition of claim 1, further comprising at least one thickening agent.

6. The composition of claim 5, wherein the at least one thickening agent is selected from the group consisting of: hydroxyethylcellulose and cetyl hydroxyethylcellulose.

7. The composition of claim 1, further comprising at least one foaming agent.

8. The composition of claim 7, wherein the at least one foaming agent is selected from the group consisting of: cocamidopropyl hydroxysultaine, lauryl hydroxysultaine, cocamine oxide, coconut fatty alcohol polyglycol ethers with ethylene oxide (EO) units ranging between 2 and 30, C8-C22 alkyl glucosides, decyl glucoside, lauryl glucoside, coco glucoside, maltooligosyl glucoside, C8-C16 alkyl polyglucosides, oligomeric D-glucopyranose, C8-C16 alkyl glycosides, C8-C22 alkyl maltosides, n-Dodecyl-β-D-maltopyranoside (DDM), cocamide MIPA and cocamide DIPA.

9. The composition of claim 1, further comprising at least one skin conditioner.

10. The composition of claim 9, wherein the at least one skin conditioner is allantoin.

11. The composition of claim 1, further comprising at least one fragrance agent.

12. The composition of claim 11, wherein the at least one fragrance agent is selected from the group consisting of: amyl acetate, isoamyl acetate and hexyl acetate.

13. The composition of claim 1, wherein the water is a solvent and the composition further comprises at least one co-solvent.

14. The composition of claim 13, wherein the at least one co-solvent is selected from the group consisting of: hexylene glycol, ethanol and 1-propanol.

15. The composition of claim 1, further comprising at least one chelating agent.

16. The composition of claim 15, wherein the at least one chelating agent is selected from the group consisting of: diammonium EDTA, disodium EDTA, tetrasodium EDTA, ethylenediamine-N,N'-disuccinic acid (EDDS), citric acid, methylglycinediacetic acid, α-alaninediacetic acid, N,N-bis(carboxymethyl)-L-glutamic acid (GLDA) and L-glutamic acid N,N diacetic acid.

17. The composition of claim 1, further comprising at least one deodorizing agent.

18. The composition of claim 17, wherein the at least one deodorizing agent is soyethyl morpholinium ethosulfate.

19. The composition of claim 1, wherein the at least two cationic ingredients comprise at least three cationic ingredients selected from the group consisting of: Polyquaternium-1, Polyquaternium-10, Polyquaternium-70, soyethyl morpholinium ethosulfate, cocamine oxide and Quaternium-Λ.

20. The composition of claim 1, wherein the at least two nonionic ingredients comprise cocamidopropyl hydroxysultaine and cetyl hydroxyethylcellulose.

21. The composition of claim 1, wherein the at least two cationic ingredients are from 1 wt. % to 20 wt. % of the total weight of the composition.

\* \* \* \* \*

UNITED STATES PATENT AND TRADEMARK OFFICE
CERTIFICATE OF CORRECTION

| | | |
|---|---|---|
| PATENT NO. | : 10,611,986 B1 | Page 1 of 2 |
| APPLICATION NO. | : 16/352036 | |
| DATED | : April 7, 2020 | |
| INVENTOR(S) | : Gary E. Schultz | |

It is certified that error appears in the above-identified patent and that said Letters Patent is hereby corrected as shown below:

On the Title Page

Item (54), and in the Specification, Column 1, Lines 1-2, delete "CLEANING COMPOSITION WITH CATIONIC SURFACTANTS" and insert --CLEANING COMPOSITION COMPRISING A CATIONIC/NONIONIC MIXTURE--.

In the Drawings

On Sheet 1 of 14, FIG. 1:, Line 16, delete "Disodium lauroaphodiacetate" and insert --Disodium lauroamphodiacetate--.

On Sheet 1 of 14, FIG. 1:, Line 19, delete "laurylglucosides" and insert --lauryl glucosides--.

On Sheet 2 of 14, FIG. 2:, Line 11, delete "Laramide DEA" and insert --Lauramide DEA--.

On Sheet 2 of 14, FIG. 2:, Line 19, delete "PET-7" and insert --PEG-7--.

On Sheet 2 of 14, FIG. 2:, Line 21, delete "Sorbital-" and insert --Sorbitol- --.

On Sheet 5 of 14, FIG. 4B:, Line 1, Component Number 19, delete "Acetamidopropyltrimonium" and insert --Acetamido propyl trimonium--.

On Sheet 6 of 14, FIG. 4C:, Line 1, Component Number 19, delete "Acetamidopropyltrimonium" and insert --Acetamido propyl trimonium--.

In the Specification

In Column 2, Line 19, delete "acetamidopropyltrimonium" and insert --acetamido propyl trimonium--.

Signed and Sealed this
Eighteenth Day of January, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,611,986 B1

In Column 6, Line 33, delete "(BO)" and insert --(EO)--.

In Column 6, Line 60, delete "(BO)" and insert --(EO)--.

In Column 7, Line 2, delete "1 wt, %" and insert --1 wt. %--.

In Column 7, Line 26, delete "5 wt, %" and insert --5 wt. %--.

In Column 7, Line 34, delete "methyiglycinediacetic" and insert --methylglycinediacetic--.

In Column 8, Line 58, delete "only," and insert --"only."--.

In Column 9, Line 6, delete "("GRAS")," and insert --("GRAS").--.

In Column 9, Line 9, delete "etc.)," and insert --etc.).--.

In Column 9, Lines 27-28, delete "concern," and insert --concern.--.

In Column 12, Line 16, delete "du Noy" and insert --du Nouy--.

In the Claims

In Column 15, Line 26, Claim 4, delete "60 wt, %" and insert --60 wt. %--.

In Column 16, Line 25 (Approx.), Claim 16, delete "N,N diacetic acid." and insert --N,N'- diacetic acid.--.